(12) United States Patent
Gokaraju et al.

(10) Patent No.: US 10,286,023 B2
(45) Date of Patent: May 14, 2019

(54) COMPOSITIONS COMPRISING NON-ACIDIC BOSWELLIA OIL FRACTION AS A BIO-ENHANCER FOR ENHANCING BIOAVAILABILITY OF BIOLOGICAL AGENTS

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Venkata Krishna Raju Alluri, Vijayawada (IN)

(73) Assignee: LAILA NUTRACEUTICALS, Vijayawada, Andhra Pradesh (IN)

( * ) Notice: Subject to any disclaimer, the term of this patent is extended or adjusted under 35 U.S.C. 154(b) by 819 days.

(21) Appl. No.: 13/689,478

(22) Filed: Nov. 29, 2012

(65) Prior Publication Data

US 2013/0084348 A1 Apr. 4, 2013

Related U.S. Application Data

(63) Continuation-in-part of application No. 13/062,066, filed as application No. PCT/IN2009/000505 on Sep. 14, 2009, now Pat. No. 9,101,599, application No. 13/689,478, which is a continuation-in-part of application No. 13/584,099, filed on Aug. 13, 2012, now Pat. No. 8,551,496, which is a continuation-in-part of application No. PCT/IN2011/000170, filed on Mar. 14, 2011, application No. 13/689,478, which is a continuation-in-part of application No. PCT/IN2011/000364, filed on May 26, 2011.

(30) Foreign Application Priority Data

Sep. 15, 2008 (IN) ............................ 2229/CHE/2008
Mar. 15, 2010 (IN) ............................. 687/CHE/2010
May 30, 2010 (IN) ............................. 688/CHE/2010

(51) Int. Cl.
*A61K 36/324* (2006.01)

(52) U.S. Cl.
CPC ................................. *A61K 36/324* (2013.01)

(58) Field of Classification Search
None
See application file for complete search history.

(56) References Cited

U.S. PATENT DOCUMENTS

| | | | |
|---|---|---|---|
| 4,499,076 A | * | 2/1985 | Ohashi |
| 5,629,351 A | | 5/1997 | Taneja et al. |
| 5,720,975 A | * | 2/1998 | Etzel .................... A61K 36/324 424/464 |
| 2003/0185907 A1 | * | 10/2003 | Krumhar ............... A61K 36/324 424/725 |
| 2003/0199581 A1 | | 10/2003 | Seligson et al. |
| 2004/0037903 A1 | | 2/2004 | Lemmo et al. |
| 2004/0073060 A1 | | 4/2004 | Gokaraju et al. |
| 2004/0166182 A1 | * | 8/2004 | Zhang .................... A61K 31/19 424/764 |
| 2004/0202709 A1 | | 10/2004 | Kirby et al. |
| 2005/0123559 A1 | | 6/2005 | Majeed et al. |
| 2006/0040000 A1 | | 2/2006 | Gokaraju et al. |
| 2006/0062859 A1 | | 3/2006 | Blum et al. |
| 2006/0089409 A1 | | 4/2006 | Gokaraju et al. |
| 2006/0246115 A1 | * | 11/2006 | Rueda ..................... A23L 1/296 424/439 |
| 2006/0275511 A1 | | 12/2006 | Murdock et al. |
| 2006/0280811 A1 | | 12/2006 | Bobardelli |
| 2007/0281045 A1 | | 12/2007 | Tripp et al. |
| 2008/0132465 A1 | | 6/2008 | Gokaraju et al. |
| 2008/0275117 A1 | | 11/2008 | Li et al. |
| 2008/0292736 A1 | | 11/2008 | Qazi et al. |
| 2008/0317885 A1 | | 12/2008 | Baker |
| 2009/0318551 A1 | | 12/2009 | Gokaraju et al. |

FOREIGN PATENT DOCUMENTS

| | | | |
|---|---|---|---|
| JP | 59013726 A | * | 1/1984 |
| JP | 06009479 A | * | 1/1994 |
| WO | 0215916 | | 2/2002 |
| WO | 2008036932 | | 3/2008 |

OTHER PUBLICATIONS

Saxena et al. Indian J Physiol Pharmacol. Oct.-Dec. 1984;28(4):299-305 (abstract only).*
Rose et al. "Frankincense Profile a scent from the bible". Internet Archive date: Apr. 8, 2005 [Retrieved from the Internet on: Jul. 9, 2016]. Retrieved from: <URL: https://web.archive.org/web/20050408221352/http://www.aromaticplantproject.com/articles_archive/frankincense_profile.html>.*
Earnst et al. "Indian Frankincense" from "Complimentary therapies for pain management" (2007), p. 208.*
Song et al. "A chemical family-based strategy for uncovering hidden bioactive molecules and multicomponent interactions in herbal medicines". Scientific Reports. pp. 1-15. (Year: 2016).*
Che et al. Molecules. 18, 5125-5141. (Year: 2013).*
Y.J. et al. Pak J Pharm Sci. Apr;19(2):129-33. (Year: 2006).*

(Continued)

*Primary Examiner* — Amy L Clark
(74) *Attorney, Agent, or Firm* — Kramer Amado, P.C.

(57) ABSTRACT

The invention relates to a non-acidic *Boswellia* low polar gum resin extract fraction (BLPRE) in combination with biological agents for enhancing the bioavailability of the biological agents. The invention also provides composition(s) comprising a *Boswellia* low polar gum resin extract (BLPRE) in combination with a biological agent for increasing the bioavailability of biological agent.

14 Claims, 5 Drawing Sheets

(56) References Cited

OTHER PUBLICATIONS

Baser, S. Phytochemical Investigations on *Boswellia* Species, University of Hamburg (online), Mar. 18, 2005, pp. 1-256, retrieved from the Internet: (http://www.boswellness.com/sites/default/files/pdfs/DissertationBasar.pdf) on Nov. 20, 2012.

Al-Harrasi et al., Phytochemical Analysis of the Essential Oil from Botanically Certified Oleogum Resin of Boswellia Sacra (Omani Luban). Molecules. Sep. 16, 2008. vol. 13, No. 9, pp. 2181-2189.

Ehrman et al., Phytochemical Databases of Chinese Herbal Constituents and Bioactive Plant Compounds with Known Target Specificities. Journal of Chemical Information and Modelling, Jan. 9, 2007. vol. 47, No. 2, pp. 254-263.

Cuaz-Perolin et al., Antiinflammatory and Antiatherogenic Effects of the NF-kB Inhibitor Acetyl-11-Keto-B-Boswellic Acid in LPS-Challenged ApoE_/_Mice, Arterioscier Thromb Vasc Biol. 2008; 28;272-277.

Kimmatkar et al., Efficacy and tolerability of Boswellia serrata extract in treatment of osteoarthritis of knee—A randomized double blind placebo controlled trial. Phytomedicine 10: 3-7 (2003).

Ernst, Frankincense:systematic review. BMJ 2008; 337:a2813.

Safayhi et al., Inhibition by Boswellic Acids of Huma Leukocyte Elastase, Journal of Pharmacology and Experimental Therapeutics 281:460-463. 1997.

Sailer et al., Acetyl-11-keto-B-boswellic acid (AKBA): structure requirements for binding and 5-lipoxygenase inhibitory activity. British Journal of Pharmacology, (1996) 117, 615-618.

Menon et al., Analgesic and psychopharmacological effects of the gum resin of Boswellia Serrata. Planta Med., 1971; 19:333-341.

Gupta et al., Effects of Boswellia Serrata Gum Resin in Patients With Brochial Asthma: Results of a Double-Blind, Placebo controlled, 6-week Clinical Study. European Journal of Medical Research. Nov. 17, 1998, 3, p. 511-514.

Gupta et al., Effects of Gum Resin of Boswellia serrata in Ptients with Chronic Colitis. Planta Med 67 (2001) 391-395.

Berg et al., The Additive Contribution from Inflammatory Genetic Markers on the Severity of Cardiovascular Disease. Scandinavian Journal of Immunology 69,(2009) 36-42.

Knight at al., Protease-activated receptors in human airways:Upregulation of PAR-2 in respiratory epithelium from patients with asthma. J. Allergy Clin Immunol, Nov. 2001. vol. 108 No. 5. pp. 797-803.

Mancini et al., 5-Lipoxygenase-activating protein is an arachidonate binding protein. 1993 Federation of European Biochemical Societies vol. 318, No. 3, pp. 277-281.

Moussaieff et al., Incensole Acetate, a Novel Anti-Inflammatory Compund Isolated from Boswellia REsin, Inhibits Nuclear Factor KB Activation. Molecular Pharmacology. 72: 1657-1664, 2007.

Pungle et al., Immonomodulatory activity of boswellic acids of Boswellia serrata Roxb. Indian Journal of Experimental Biology. vol. 41, Dec. 2003 pp. 1460-1462.

Roy et al., Regulation of Vascular Responses to Inflammation: Inducible Matrix Metalloproteinase-3 Expression in Human Microvascular Endothelial Cells Is Sensitive to Antiinflammatory Boswellia. Antioxidants & Redox Signaling. vol. 8, Nos. 3&4, 2006, pp. 653-660.

Roy et al., Human Genome Screen to Identify the Genetic Basis of the Anti-infalmmatory Effects of Boswellia in Microvascular Endothelial Cells. DNA and Cell Biology. vol. 24, No. 4, 2005, pp. 244-255.

Zutshi, Mechanism of Cholesterol Lowering Effect of Salai Guggal Ex. Bosellia Serrata Roxb., Indian J. Pharmac.—18:182-183.1986.

International Search Report dated Dec. 1, 2011 for PCT/IN2011/000364.

\* cited by examiner

2 R₁ = OH and R₂ = H
3 R₁ = H and R₂ = OH

COMPOSITIONS COMPRISING NON-ACIDIC BOSWELLIA OIL FRACTION AS A BIO-ENHANCER FOR ENHANCING BIOAVAILABILITY OF BIOLOGICAL AGENTS

This application is a continuation-in-part of U.S. nonprovisional patent application Ser. No. 13/062,066, filed on Mar. 3, 2011, which is a national stage application based on international application PCT/IN2009/000505, filed Sep. 14, 2009, which claims priority to Indian patent application 2229/CHE/2008, filed Sep. 15, 2008; and also a continuation-in-part of U.S. nonprovisional patent application Ser. No. 13/584,099, filed on Aug. 13, 2012, which is a continuation-in-part of international application PCT/IN2010/000233, published as WO 2011/099029, filed on Apr. 12, 2010, which claims priority to Indian patent application 384/CHE/2010, filed Feb. 15, 2010. This application is additionally a continuation-in-part of international application PCT/IN2011/000364, filed on May 26, 2011, which claims priority to Indian patent application 688/CHE/2010, filed May 30, 2010. The entire disclosures of the prior applications are hereby incorporated by reference in their entirety.

FIELD OF THE INVENTION

The invention provides non-acidic *Boswellia* low polar gum resin extract fraction (BLPRE), *Boswellia* volatile oil fraction (BVOIL) or *Boswellia* oil fraction (BOIL) comprising BLPRE and BVOIL for increasing the bioavailability of biological agents.

The present invention provides composition(s) comprising at least one component selected from *Boswellia* oil (BOIL), *Boswellia* volatile oil (BVOIL) and *Boswellia* low polar gum resin extract (BLPRE) in combination with a biological agent for increasing the bioavailability of the biological agent.

OBJECTIVE OF THE INVENTION

There are numerous pharmaceutical, herbal ingredients and biologically active molecules that are effective in vitro against a disease condition or disorder. However, several of them are not effective or not bioavailable in vivo (warm blooded animals). It is thus important to explore, identify and invent safe and effective agents that help to increase the bioavailability of such ingredients. In the present disclosure, a number of herbal ingredients are shown to enhance bioavailability of biologically active materials.

BACKGROUND OF THE INVENTION

The gum resin of *Boswellia* has been very widely used since ancient times. For example, the gum resin of *Boswellia serrata* (Burseraceae) has long been in use for the treatment of rheumatoid arthritis and gout by the practitioners of Ayurvedic medicines in the Indian system of medicine. Various extracts of the gum resin have shown potent anti-inflammatory and anti-atherogenic activity in laboratory animals. The extract of *Boswellia* was found to be a potent anti-arthritic agent. *Boswellia* gum resin and its extracts also demonstrated significant therapeutic improvements inhuman clinical trials thus confirming the in vivo anti-inflammatory effects.

The origin of the anti-inflammatory action of *Boswellia* gum resin and its extracts has been attributed to a group of triterpene acids called Boswellic acids that were isolated from the gum resin of *Boswellia serrata*. Boswellic acids exert anti-inflammatory actions by inhibiting 5-lipoxygenase (5-LOX). 5-LOX is a key enzyme for the biosynthesis of leukotrienes from arachidonic acid. Leukotrienes are considered to be involved in the initiation and propagation of a variety of inflammatory diseases. In addition to their 5-lipoxygenase inhibition, Boswellic acids inhibit human leukocyte elastase (HLE), an enzyme of different pro-inflammatory pathway. 3-O-Acetyl-11-keto-β-Boswellic acid (AKBA) is biologically the most active component among its congeners, with an $IC_{50}$ of 1.5 µM for the inhibition of 5-LOX.

The U.S. Pat. Nos. 5,716,928 and 5,665,386 relate to a method for increasing bioavailability of an orally administered hydrophobic pharmaceutical compound, which comprises orally administering the pharmaceutical compound to a mammal in need of treatment with the compound concurrently with an essential oil or essential oil component in an amount sufficient to enhance bioavailability of the compound. Specifically, bioavailability of the compound in the presence of the essential oil or essential oil component is greater than bioavailability of the compound in the absence of the essential oil or essential oil component. The essential oil or essential oil component has an activity of at least 10% inhibition at a concentration of 0.01 wt. % or less, in an assay that measures reduced conversion of cyclosporine to hydroxylated products using an assay system containing 250 µg rat liver microsomes, 1 µM cyclosporine and 1 mM reduced nicotinamide adenine dinucleotide phosphate (NADPH) in 1 ml of 0.1 M sodium phosphate buffer, pH 7.4.

PCT publication WO 02/15916 discloses dihydro *Boswellia* acids, physiologically acceptable salts thereof and hydrogenated extracts from *Boswellia*. These compounds are useful for the prophylactic and/or therapeutic treatment of undesired physical and psychic conditions, in particular of somatic, psychosomatic and psychic diseases, such as inflammatory processes caused by increased leukotriene formation, leukocyte elastase or plasmin activity.

There is, however, no prior art, to the best of inventors knowledge, relating to the use of non-acidic *Boswellia* gum resin extract fractions for increasing the bioavailability of biological agents in warm blooded animals.

Approximately 30 percent of older Americans do not get the dietary requirements of all the essential nutrients. The hazards of food-drug interactions in depleting essential nutrients are well recognized. It is unavoidable that old age calls for increased use of medications. For example, use of certain antibiotics decreases absorption of calcium and iron, while EDTA chelation therapy decreases absorption of zinc, iron, copper, and magnesium.

In addition, many foods which increase the risk of cancer and cardiovascular disease have to be eliminated from the diet, which further depletes the sources of essential nutrients. For example, excellent sources of vitamin B and vitamin D, such as red meat, liver, egg yolk, cheese and dairy products, are often limited because of their high cholesterol content.

Limited menu also causes a depletion of essential amino acids, such as tryptophan, which is important precursor of neurotransmitters, and may play a role in the prevention of brain deterioration with aging. The availability of essential nutrients is further compromised by poor gastrointestinal absorption.

The traditional way to offset insufficient nutrient supplementation, insufficient gastrointestinal absorption and insufficient metabolic utilization of essential nutrients is to administer large doses of compensating materials, such as vitamin and mineral supplements.

Hence, there exists a great need for the development of a compound/composition which helps in increasing the availability of biological agents through one or more mechanisms comprising increasing the bioavailability, increasing the serum concentration, improving gastrointestinal absorption, improving systemic utilization, improving cross over through certain biological barriers such as respiratory lining, urinary lining, blood brain barrier and skin in warm blooded animals.

SUMMARY OF THE INVENTION

In a first aspect the invention provides *Boswellia* oil (BOIL) for increasing the bioavailability of biological agents.

In another aspect, the invention provides *Boswellia* volatile oil fraction (BVOIL) for increasing the bioavailability of biological agents.

In a further aspect, the invention provides *Boswellia* low polar gum resin extract fraction (BLPRE) for increasing the bioavailability of biological agents.

In another aspect the invention provides compositions comprising at least one component selected from *Boswellia* oil (BOIL), *Boswellia* volatile oil (BVOIL) and *Boswellia* low polar gum resin extract (BLPRE) obtained from *Boswellia* gum resin in combination with a biological agent, for increasing the bioavailability of biological agent in warm blooded animals in need thereof.

In another aspect the invention provides *Boswellia* derived bioenhancing agents for increasing the bioavailability of one or more biological ingredients or functional ingredients.

In another aspect the invention provides *Boswellia* derived bioenhancing agents for increasing the bioavailability of one or more pharmaceutical drugs/synthetic drugs.

In another aspect the invention provides *Boswellia* derived bioenhancing agents for increasing the bioavailability of one or more *Boswellia* derived components.

In another aspect the invention provides *Boswellia* derived bioenhancing agents for increasing the bioavailability of one or more *Curcuma* derived components.

DETAILED DESCRIPTION OF THE INVENTION

Figure 1:
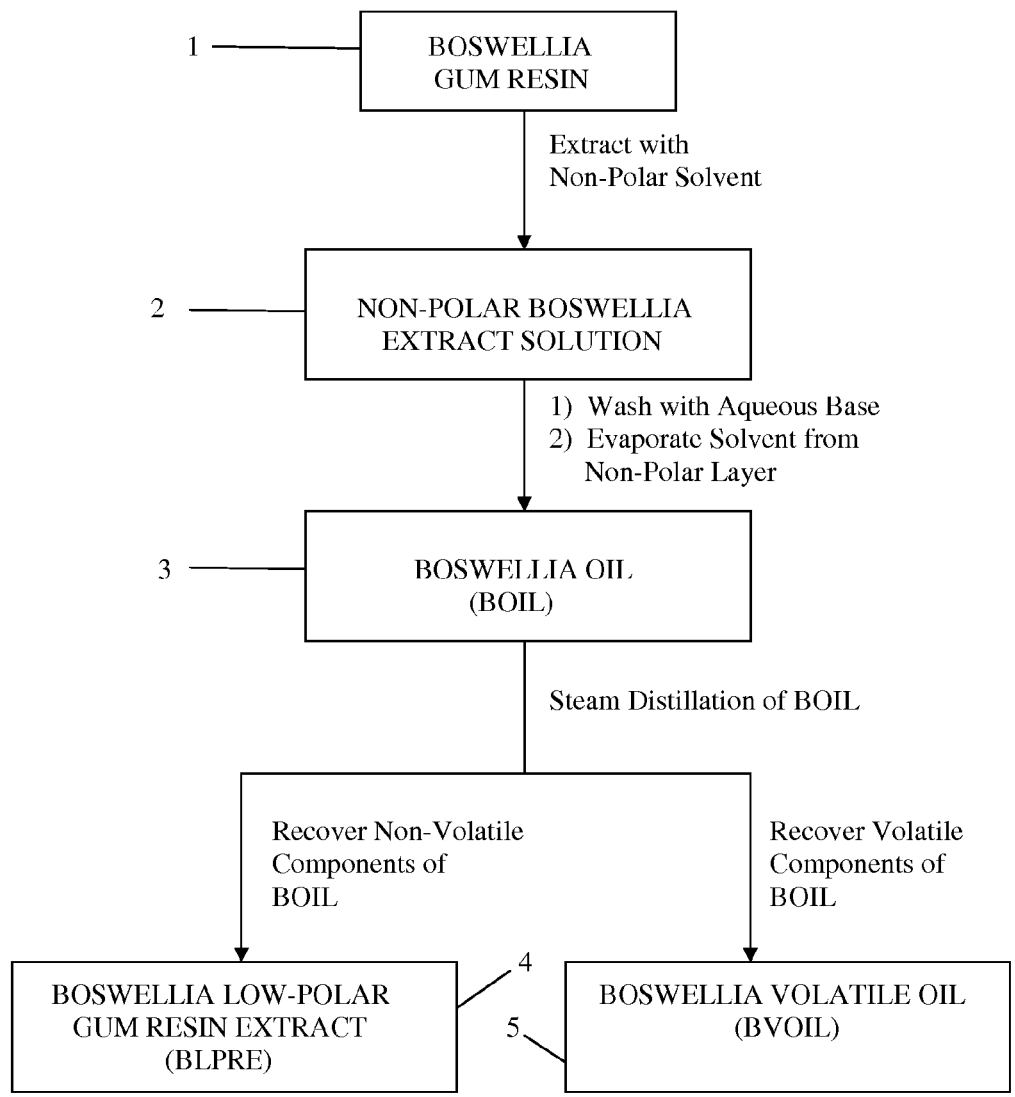
FIGS. 1 and 2 show processes for obtaining BLPRE, BOIL, and BVOIL.

1. '*Boswellia* oil' or 'non-acidic *Boswellia* extract' or 'BOIL' used herein refers to a non-acidic *Boswellia* gum resin extract containing a non-acidic *Boswellia* low polar gum resin extract fraction (BLPRE) and a *Boswellia* volatile oil fraction (BVOIL) obtained from gum resin of any of the *Boswellia* species.

2. '*Boswellia serrata* oil' or 'non-acidic *Boswellia serrata* extract' or 'BsOIL' used herein refers to non-acidic *Boswellia serrata* gum resin extract containing non-acidic *Boswellia serrata* low polar gum resin extract fraction (BsLPRE) and *Boswellia serrata* volatile oil fraction (BsVOIL) obtained from gum resin of the *Boswellia serrata* species.

3. '*Boswellia carterii* oil' or 'non-acidic *Boswellia carterii* extract' or 'BcOIL' used herein refers to non-acidic *Boswellia carterii* gum resin extract containing non-acidic *Boswellia carterii* low polar gum resin extract fraction (BcLPRE) and *Boswellia carterii* volatile oil fraction (BcVOIL) obtained from gum resin of the *Boswellia carterii* species.

4. '*Boswellia* low polar gum resin extract fraction' or '*Boswellia* low polar gum resin extract' or 'BLPRE' used herein refers to non-acidic *Boswellia* gum resin extract oil fraction comprising sesquiterpenes, diterpenes, triterpenes and other oily phytochemicals obtained after removing the volatile components from *Boswellia* oil obtained from gum resin of any of the *Boswellia* species by any of the processes described.

5. '*Boswellia serrata* low polar gum resin extract fraction' or '*Boswellia serrata* low polar gum resin extract' or 'BsLPRE' used herein refers to non-acidic *Boswellia serrata* gum resin extract oil fraction comprising sesquiterpenes, diterpenes, triterpenes and other oily phytochemicals obtained after removing the volatile components from *Boswellia* oil obtained from gum resin of *Boswellia serrata* species by any of the processes described.

6. '*Boswellia carterii* low polar gum resin extract fraction' or '*Boswellia carterii* low polar gum resin extract' or 'BcLPRE' used herein refers to non-acidic *Boswellia carterii* gum resin extract oil fraction comprising sesquiterpenes, diterpenes, triterpenes and other oily phytochemicals obtained after removing the volatile components from *Boswellia carterii* oil obtained from gum resin of *Boswellia carterii* species by any of the processes described.

7. '*Boswellia* volatile oil fraction' or '*Boswellia* volatile oil' or 'volatile oil' or 'volatile fraction' or 'BVOIL' used herein refers to the volatile fraction/extract comprising monoterpenes, sesquiterpenes, volatile oils and other oily phytochemicals obtained from gum resin of any of the *Boswellia* species by any of the processes described.

8. '*Boswellia serrata* volatile oil fraction' or '*Boswellia serrata* volatile oil' or 'serrata volatile oil' or 'serrata volatile fraction' or 'BsVOIL' used herein refers to the volatile fraction/extract comprising monoterpenes, sesquiterpenes, volatile oils and other oily phytochemicals obtained from gum resin of the *Boswellia serrata* species by any of the processes described.

9. '*Boswellia carterii* volatile oil fraction' or '*Boswellia carterii* volatile oil' or 'carterii volatile oil' or 'carterii volatile fraction' or 'BcVOIL' used herein refers to the volatile fraction/extract comprising monoterpenes, sesquiterpenes, volatile oils and other oily phytochemicals obtained from gum resin of the *Boswellia carterii* species by any of the processes described.

10. 'Gum' or 'Gum resin' or 'resin' used herein refers to an exudate of *Boswellia* plant species.

11. 'Phytochemical' refers to a pure or semi-pure compound or compounds isolated from plants.

12. 'Bioenhancer(s)' refers to agents that enhance the availability of biological agent(s) through one or more mechanism(s) in warm blooded animals comprising increasing the bioavailability, enhancing the serum concentration, improving gastrointestinal absorption, improving systemic utilization, improving cross over through certain biological barriers such as respiratory lining, urinary lining, blood brain barrier and skin.

13. 'Bioenhancing composition(s)' refer to compositions comprising *Boswellia* derived oil fraction as Bioenhancer in combination with one or more biological agent(s).

14. 'Biological agent(s)' refer to one or more agents selected from biologically active ingredient(s), functional ingredient(s), anti-oxidant(s), vitamin(s), mineral(s), amino acid(s), and oil(s) their mixtures obtained from plant(s)/animal(s)/microorganism(s)/synthesis and semi synthesis.

15. 'BSE 85%' used herein refers to *Boswellia serrata* extract standardized to 85% Boswellic acids.

16. 'BCE 85%' used herein refers to *Boswellia carterii* extract standardized to 85% Boswellic acids.

17. 'CLE 95%' refers to *Curcuma longa* extract standardized to 95% Curcuminoids.

18. 'CAE 20%' refers to *Curcuma aromatica* extract standardized to 20% Curcuminoids.

19. 'Biologically active ingredient(s)' refers to any pharmaceutically or nutraceutic ally or dietetically acceptable active ingredient(s); compound(s), extract(s), fraction(s), phytochemical(s), synthetic drug(s) or their salts or mixtures thereof derived from plants or animals or microorganisms or chemical synthesis or semi-synthesis.

20. 'Functional ingredient(s)' refers to any herbal ingredients, dietary supplements, antioxidants, vitamins, minerals, amino acids, fatty acids, essential oils, fish oils, enzymes, glucosamine, Chondroitin and probiotics or their salts or mixtures thereof derived from plants or animals or microorganisms or chemical synthesis or semi-synthesis.

The gum resin of *Boswellia* has been very widely used since ancient times. The gum resin of various species of *Boswellia* such as *Boswellia serrata, Boswellia carterii* or *Boswellia papyrifera* is a complex mixture comprising *Boswellia* oil fraction (BOIL) containing essential oil/*Boswellia* volatile oil fraction (BVOIL) and non-acidic *Boswellia* low polar gum resin extract fraction (BLPRE); boswellic acids, sugars and polysaccharide fraction. The *Boswellia serrata/Boswellia carterii/Boswellia papyrifera* extracts widely available in the international markets are acidic fractions separated from the gum resin which are standardized to contain 65% or 85% total Boswellic acids by titrimetric method of analysis. During the execution of commercial process for regular *Boswellia* extracts derived from *Boswellia serrata/Boswellia carterii/Boswellia papyrifera* (85% total Boswellic acids), the acidic fraction, which contains predominantly triterpene acids including Boswellic acids is separated from the rest of gum resin components. The sugars and other polymeric materials get separated out into the aqueous phase during the enrichment process for total Boswellic acids. The remaining water immiscible low polar compounds are separated as *Boswellia* oil fraction/extract. These low polar compounds are either absent or present at very low concentration in both, commercial *Boswellia* extracts standardized to boswellic acids and *Boswellia* extracts selectively enriched in 3-O-acetyl-11-keto-β-Boswellic acid (AKBA).

The *Boswellia* non-acidic oil fractions BOIL, BVOIL, and BLPRE may be obtained in a number of ways. One method of obtaining the *Boswellia* non-acidic oil fractions BOIL, BVOIL, and BLPRE is outlined in FIG. 1. According to this method, *Boswellia* gum resin 1 is extracted with a non-polar or water-immiscible solvent to produce a solution of an extract of *Boswellia* gum resin 2 in a non-polar solvent. The non-polar solvent may be a non-polar organic solvent, such as 1,2-dichloroethane, hexane, dichloromethane, chloroform, ethyl acetate, n-butanol, or methyl iso-butyl ketone (MIBK). Alternatively, the non-polar solvent may be a non-polar inorganic solvent. The non-polar extract solution 2 is then washed with an aqueous base to extract boswellic acids and other acidic components into an aqueous layer, leaving a non-polar solvent layer containing non-acidic components of the extract of *Boswellia* gum resin. The non-polar solvent is then evaporated to produce a *Boswellia* oil (BOIL) 3, which contains volatile components and non-volatile components. BOIL 3 is subjected to steam distillation to volatilize the volatile components of BOIL 3. After removal of the volatile components from BOIL 3, the remaining non-volatile oil, here referred to as *Boswellia* low-polar gum resin extract (BLPRE) 4, may be recovered. Similarly, after steam distillation, the volatile components from BOIL 3 may be condensed or otherwise recovered as a *Boswellia* volatile oil (BVOIL) 5. Thus, BOIL 3 contains both volatile and non-volatile compounds. BLPRE 4 contains non-volatile compounds. BVOIL 5 contains only volatile compounds.

An alternative method of obtaining the *Boswellia* non-acidic oil fractions BOIL, BVOIL, and BLPRE is outlined in FIG. 2. According to this method, *Boswellia* gum resin 1 is extracted with a polar solvent, which may be alcohol or aqueous alcohol. The resulting polar *Boswellia* extract 6 is portioned between an aqueous base solution and a non-polar solvent to produce an aqueous layer and a non-polar solvent layer of a solution of an extract of *Boswellia* gum resin 7 in a non-polar solvent. The aqueous layer may be discarded. The non-polar solvent may be a non-polar organic solvent, such as 1,2-dichloroethane, hexane, dichloromethane, chloroform, ethyl acetate, n-butanol, or methyl iso-butyl ketone (MIBK). Alternatively, the non-polar solvent may be a non-polar inorganic solvent. The non-polar solvent is then evaporated from non-polar extract solution 7, leaving a *Boswellia* oil (BOIL) 3, which contains volatile components and non-volatile components. BOIL 3 is subjected to vacuum to volatilize the volatile components of BOIL 3. After removal of the volatile components from BOIL 3, the remaining non-volatile oil, here referred to as *Boswellia* low-polar gum resin extract (BLPRE) 4, may be recovered. Similarly, after steam distillation, the volatile components from BOIL 3 may be condensed or otherwise recovered as a *Boswellia* volatile oil (BVOIL) 5.

Process for obtaining non-acidic *Boswellia* oil (BOIL) fraction:

A representative process for obtaining *Boswellia* oil comprises:

a) procuring the gum resin of one or more of the plant(s) selected from but not limited to *Boswellia serrata* or *Boswellia carterii* or *Boswellia papyrifera* or mixtures thereof, b) extraction of the gum resin with a water immiscible organic solvent, c) filtering the extract carefully to remove the insoluble resin material, d) washing the organic solvent extract repeatedly with an aqueous alkali solution such as aqueous potassium hydroxide, e) washing the organic layer with water and brine and, f) evaporating the organic layer under vacuum and high temperature to obtain the oily residue (BOIL).

Processes for Obtaining *Boswellia* Volatile Oil (BVOIL) Fraction:

The process for obtaining *Boswellia* volatile oil (BVOIL) is through steam distillation or using high vacuum from *Boswellia* gum resin.

A representative process for obtaining *Boswellia* volatile oil comprises:

a) procuring the gum resin of *Boswellia* and b) separating the Volatile oil component by either steam distillation or distillation under high vacuum, low temperature from the said gum resin to obtain BVOIL.

In an alternative process, a) BOIL is prepared according to the process described above, b) BOIL is then subjected to steam distillation or vacuum distillation to collect *Boswellia* volatile oil (BVOIL).

Processes for Obtaining *Boswellia* Low Polar Gum Resin Extract (BLPRE) Fraction:

A representative procedure for obtaining *Boswellia* low polar gum resin extract (BLPRE) comprises:

a) extraction of the gum resin of *Boswellia* species with a water immiscible organic solvent and filtering the extract carefully to remove the insoluble resin material, b) washing the organic solvent extract repeatedly with an aqueous alkali solution such as aqueous potassium hydroxide, c) washing the organic layer obtained after the alkali wash, with water and brine, d) evaporating the said organic layer under vacuum and high temperature to obtain the oily residue and, e) removing the volatile compounds from the said oily residue under high vacuum and high temperature to obtain BLPRE.

Another representative procedure for obtaining *Boswellia* low polar gum resin extract (BLPRE) comprises:

a) preparing the alcohol or hydroalcohol extract of *Boswellia* gum resin, b) partitioning the alcohol extract between an aqueous alkali solution and a water immiscible organic solvent, c) separating of the organic solvent layer, followed by evaporation of the solvent to obtain oily residue and, d) removing of volatile compounds from the said oily residue under high temperature and high vacuum to obtain BLPRE.

Yet another representative procedure for obtaining *Boswellia* low polar gum resin extract (BLPRE) comprises:

a) extracting the gum resin of *Boswellia* species with alcohol or hydro alcohol, b) evaporating the organic solvent to an optimum level of total solids and then c) adjusting the pH to the alkaline side, preferably pH 9-12, d) repeatedly extracting the solution with an organic solvent, e) evaporating the organic solvent under vacuum and high temperature to obtain the oily residue and, f) evaporating the volatiles from the said oily residue under high vacuum and high temperature to obtain BLPRE.

A representative procedure for obtaining *Boswellia serrata* volatile oil (BsVOIL) comprises:

a) procuring the gum resin of *Boswellia serrata* and b) separating the Volatile oil component by either steam distillation or distillation under high vacuum, low temperature from the said gum resin to obtain BsVOIL.

Yet another representative procedure for obtaining *Boswellia carterii* volatile oil (BcVOIL) comprises:

a) procuring the gum resin of *Boswellia carterii* and b) separating the Volatile oil component by either steam distillation or distillation under high vacuum, low temperature from the said gum resin to obtain BcVOIL.

The representative processes for obtaining *Boswellia* volatile oil (BVOIL) from *Boswellia serrata*, *Boswellia carterii* are described above. However, a similar process or processes can be applied to any of the gum resin obtained from *Boswellia* species for producing *Boswellia* volatile oil (BVOIL).

A representative procedure for obtaining *Boswellia serrata* low polar gum resin extract (BsLPRE) comprises:

a) Procuring the gum resin of *Boswellia serrata* b) extracting with an water immiscible organic solvent and the insoluble gum materials were separated by filtration and discarded, c) washing the organic solvent extract repeatedly with dilute aqueous alkali solution to remove the acidic compounds, d) washing the organic layer successively with water and brine, e) evaporating the organic layer under vacuum at 60-70° C. to obtain an oily residue and, f) removing the volatile components are then removed from the said oily residue under high vacuum and high temperature to obtain a viscous oil, which is referred hereinafter as *Boswellia serrata* low polar gum resin extract (BsLPRE).

Alternatively, the BsLPRE can also be prepared by a process comprising:

a) preparing the alcohol or hydroalcohol extract of *Boswellia serrata* gum resin, b) partitioning the alcohol extract between an aqueous alkali solution and a water immiscible organic solvent, c) separation of the organic solvent layer, followed by evaporating the organic layer under vacuum at 60-70° C. to obtain an oily residue and, d) removing the volatile components are then removed from the said oily residue under high vacuum and high temperature to obtain a viscous oil, which is referred herein after as *Boswellia serrata* low polar gum resin extract (BsLPRE).

A representative procedure for obtaining *Boswellia carterii* low polar gum resin extract (BcLPRE) comprises:

a) procuring the gum resin of *Boswellia carterii*, b) extracting the gum resin with an water immiscible organic solvent and the insoluble gum materials were separated by filtration and discarded, c) washing the organic solvent extract repeatedly with dilute aqueous alkali solution to remove the acidic compounds, d) washing the organic layer successively with water and brine, e) evaporating the organic layer under vacuum at 60-70° C. to obtain an oily residue and f) removing the volatile components are then removed from the said oily residue under high vacuum and high temperature to obtain a viscous oil, which is referred hereinafter as *Boswellia carterii* low polar gum resin extract (BcLPRE).

Alternatively, the BcLPRE can also be prepared by process comprising:

a) preparing the alcohol or hydroalcohol extract of *Boswellia carterii* gum resin, b) partitioning the alcohol extract between an aqueous alkali solution and a water immiscible organic solvent, c) separation of the organic solvent layer, followed by evaporating the organic layer under vacuum at 60-70° C. to obtain an oily residue, d) the volatile components are then removed from the said oily residue under high vacuum and high temperature to obtain a viscous oil, which is referred herein after as *Boswellia carterii* low polar gum resin extract (BcLPRE).

The representative processes for obtaining *Boswellia* low polar gum resin extract (BLPRE) from *Boswellia serrata* and *Boswellia carterii* are described above. However, a similar process or processes can be applied to any of the gum resin obtained from *Boswellia* species for producing the low polar gum resin extract.

Figure 2:
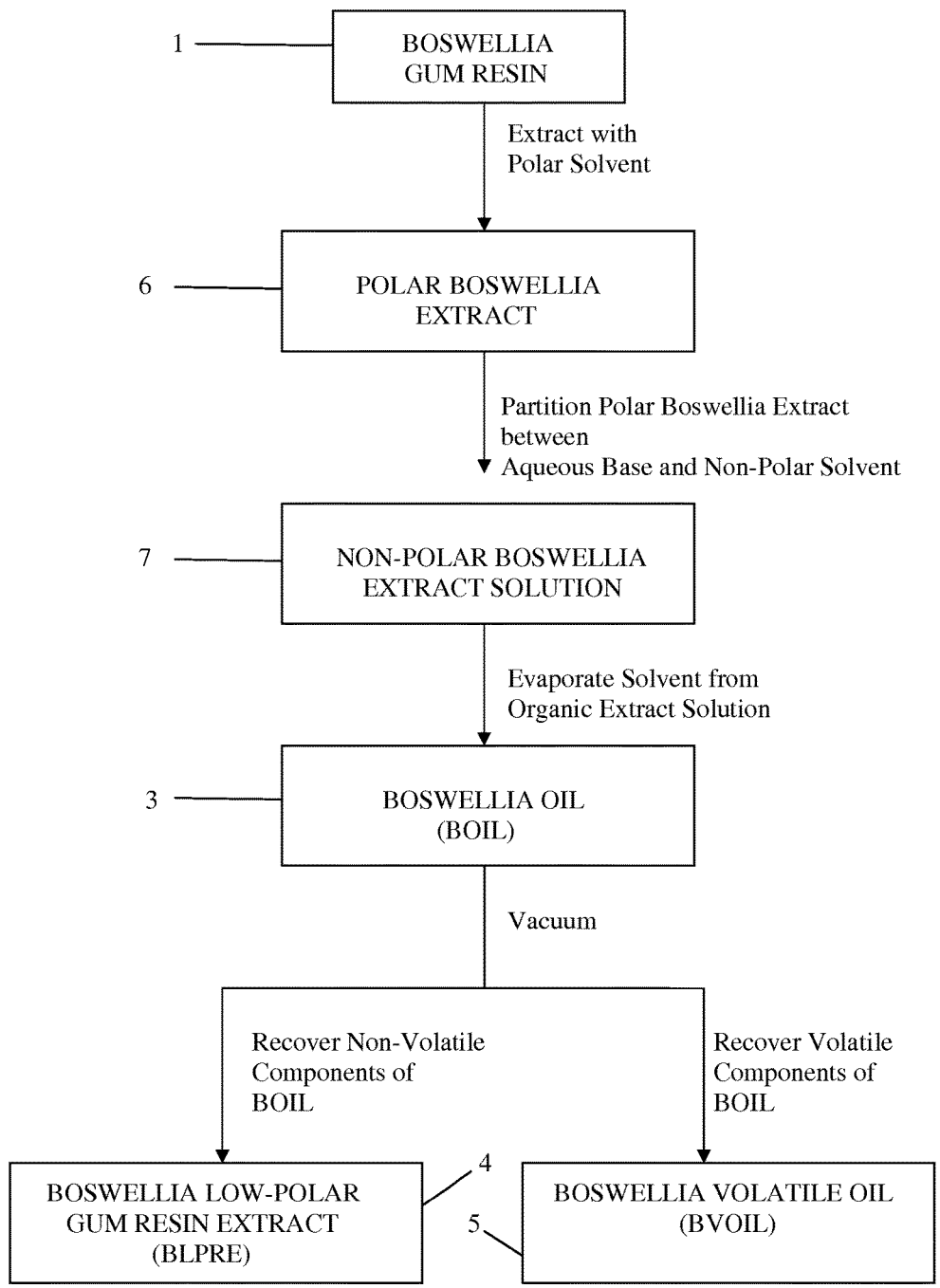

The said intact *Boswellia* oil (BOIL) or *Boswellia* volatile oil (BVOIL) or *Boswellia* low polar gum resin extract (BLPRE) constitute significant components in *Boswellia* gum resin. However, BOIL, BVOIL, and BLPRE have very limited commercial utility and are mostly discarded as a waste material. Potential utilization of these fractions has been long overdue. The current disclosure shows that an intact *Boswellia* oil (BOIL); a *Boswellia serrata* low polar gum resin extract (BsLPRE), which is the fraction obtained after removing volatile compounds from the *Boswellia serrata* oil BOIL; and a *Boswellia* volatile oil (BVOIL), a fraction comprising volatile compounds removed from BOIL, each have several beneficial properties. As shown in FIGS. 1 and 2, BVOIL and BLPRE are obtained by fractionating BOIL into volatile and non-volatile components, respectively. BOIL, BVOIL, and BLPRE may be distinguished from conventional *Boswellia* extracts in that they do not contain significant amounts of acidic compounds, such as boswellic acids.

In our earlier Indian patent application 2229/CHE/2008 filed 15 Sep. 2008 and PCT application #PCT/IN2009/000505 filed 14 Sep. 2009 we disclosed synergistic compositions comprising an AKBA enriched fraction and a *Boswellia serrata* non-acidic extract (BNRE). BNRE composition and method of identification are also disclosed.

In our recent Indian patent application 394/CHE/2010 filed 15 Feb. 2010 we disclosed non Boswellic acid fraction and its synergistic compositions.

During the search for bioenhancing agents, the inventors found that non-acidic *Boswellia* low polar gum resin extract fraction (BLPRE), *Boswellia* volatile oil fraction (BVOIL) or *Boswellia* oil fraction (BOIL) comprising BLPRE and BVOIL enhance the bioavailability of bioactive agents. The compositions LI13108F containing *Boswellia serrata* low polar gum resin extract (BsLPRE; LI13115) and *Boswellia serrata* extract selectively enriched to 30% 3-O_acetyl-11-keto-β-boswellic acid (AKBA) and LI13119F containing *Boswellia serrata* volatile oil fraction (BsVOIL) and *Boswellia serrata* extract selectively enriched to 30% 3-O_acetyl-11-keto-β-boswellic acid (AKBA) were supplemented to Albino Wistar rats. The control group of animals was supplemented with *Boswellia serrata* extract selectively enriched to 30% AKBA. Blood samples were collected from all animals prior to oral administration of test products and at 0.5, 1, 2, 4, 8 and 12 hrs after oral administration. The comparative oral bioavailability of AKBA from these *Boswellia* products was evaluated by measuring the serum AKBA concentration for each test animal using LC-MS.

Surprisingly, both the compositions LI 13108F and LI 13119F showed better oral bioavailability with AUCs 14.08 and 11.23 respectively compared to AUC 9.825 shown by individual ingredient *Boswellia serrata* extract containing 30% AKBA (LI 13115). The bioavailability (in terms of AUC) of LI 13108F is 43.33% more than LI 13115. The bioavailability of LI 13119F is 14.33% more than that of LI 13115. The study details are summarized in example-5 and depicted in FIG. 4.

To exert optimal therapeutic efficacy, an active substance should reach systemic circulation and site of its action in an effective concentration during the desired period. Improving bioavailability and reducing dosage frequency without losing therapeutic benefit is crucial in achieving therapeutic efficacy and patient compliance in chronic treatment regimes. The present invention achieves this objective by enhancing the oral bioavailability of AKBA in compositions containing BsLPRE or BsVOIL.

The bioavailability enhancing effect of BsLPRE was further confirmed by evaluating the composition LI13124F1 containing BsLPRE and a novel curcumin compound called bisdemethylcurcumin (LI01008) in comparison with LI01008 alone in Alibino Wistar rats. Bisdemethylcurcumin is a potent curcuminoid, far superior to other naturally occurring curcuminoids with respect to antioxidant and other biological activities commonly exhibited curcumins. The composition LI13124F1 showed better bioavailability of LI01008 in serum samples compared to the animals supplemented with LI01008 alone. The serum samples of animals supplemented with LI13124F1 showed 75% better bioavailability compared to the serum samples of the animals supplemented with LI01008 alone. The experimental studies are discussed in example-6 and depicted in FIG. 5.

The foregoing thus suggest that the non-acidic *Boswellia* low polar gum resin extract fraction (BLPRE), *Boswellia* volatile oil fraction (BVOIL) or *Boswellia* oil fraction (BOIL) comprising BLPRE and BVOIL enhance the bioavailability of bioactive agents. These bio-enhancing agents thus can be useful to improve the efficacy and reduce the dose of bioactive agents.

Different Embodiments of the Present Invention are as Outlined Below:

In an important aspect, the invention provides bioenhancing agents selected from intact *Boswellia* oil (BOIL), *Boswellia* volatile oil (BVOIL) and *Boswellia* low polar gum resin extract (BLPRE) obtained from *Boswellia* gum resin of *Boswellia* species for increasing the bioavailability of biological agents.

In an important aspect, the invention provides compositions comprising one or more ingredients selected from intact *Boswellia* oil (BOIL), *Boswellia* volatile oil (BVOIL) and *Boswellia* low polar gum resin extract (BLPRE) obtained from *Boswellia* gum resin of *Boswellia* species in combination with a biological agent for increasing the bioavailability of biological agent.

In another aspect, the invention provides *Boswellia* derived bioenhancing agents for improving the bioavailability and/or bio-efficacy of nutraceuticals or dietary supplements is also relevant to animal health besides being important for humans.

In another aspect the invention provides *Boswellia* derived bioenhancing agents for increasing the bioavailability of one or more biological ingredient(s) or functional ingredient(s).

In another aspect the invention provides *Boswellia* derived bioenhancing agents for increasing the bioavailability of one or more *Boswellia* derived components.

In another aspect the invention provides *Boswellia* derived bioenhancing agents for increasing the bioavailability of one or more *Curcuma longa* derived components.

In another aspect the invention provides the method of using *Boswellia* derived bioenhancing agents for enhancing the bioavailability of biological agents.

In another aspect, the invention provides bioenhancing agents, which function through one or more of the mechanisms comprising increasing the bioavailability, enhancing the serum concentration, improving gastrointestinal absorption, improving systemic utilization and improving cross over through certain biological barriers like respiratory lining, urinary lining, blood brain barrier and skin.

In another aspect, the invention provides bio-enhancing agents *Boswellia* oil (BOIL), *Boswellia* volatile oil (BVOIL) and *Boswellia* low polar gum resin extract (BLPRE) derived from the gum resin of *Boswellia* where in the gum resin can be obtained from one or more of the *Boswellia* species selected from *Boswellia serrata, Boswellia carterii* and *Boswellia papyrifera*.

In another aspect the invention provides compositions for bioenhancing the activity of biological agents in warm blooded animals in need thereof.

In another aspect the invention provides compositions comprising *Boswellia* oil (BOIL), *Boswellia* volatile oil (BVOIL) and *Boswellia* low polar gum resin extract (BLPRE) for enhancing the bioavailability of nutraceutical or dietetical ingredients in warm blooded animals in need thereof.

The nutraceutical/dietetically acceptable agents comprise one or more ingredients selected from phytochemicals, Nootropic agents, anti obese agents, antiinflammatory agents, anti cholesterol agents, anti arthritic agents, anti diabetic agents, anti microbial agents, anti fungal agents, anti cancer agents, anti hypertensive agents, analgesic agents, anti platelet aggregation agents, anti atherosclerotic agents, antioxidants, anti thrombotic agents, antibiotic agents, anti malarial agents, anti osteoporotic agents, probiotics agents, anti fungal agents, immune potentiating agents, anti viral agents, anti histamines, muscle relaxants, anti depressants, hypnotic agents and their salts thereof.

In another aspect the invention provides composition(s) for increasing the bioavailability of one or more biological ingredient(s) selected from biologically active ingredient(s), functional ingredient(s), herbal ingredient(s), dietary supplement(s), nutrient(s), anti-oxidant(s), vitamin(s), mineral(s), amino acid(s), and oil(s) their mixtures obtained from plant(s)/animal(s)/microorganism(s)/synthesis/semi-synthesis.

The functional ingredient(s) comprise one or more ingredients selected from nutrients, dietary supplements, nutritional ingredients, herbal ingredients, phytochemicals, animal proteins, glucosamine, chondroitin, plant proteins, fruit extracts, animal extracts, algae extracts, probiotics and their salts thereof.

The herbal ingredient(s) comprise one or more ingredients selected from extracts/fractions/phytochemicals and their salts derived from *Withania somnifera, Bacopa monniera, Boswellia* species, *Curcuma* species, *Centella asiatica, Sphaeranthus indicus, Annona squamosa, Holoptelia integrifolia, Piper betel, Dolichos biflorus, Moringa oleifera* and *Murraya koenigii*.

The anti-oxidant(s) comprise one or more ingredients selected from vitamin A, vitamin C, vitamin E, alpha-carotene, trans-beta-carotene, betacryptoxanthin, lycopene, lutein/zeaxanthin, pine bark bioflavonals complex, germanium, selenium and zinc.

The vitamin(s) comprise one or more water soluble vitamins selected from vitamin B1, vitamin B2, niacinamide, vitamin B6, vitamin B12, folic acid and vitamin C; fat-soluble vitamins selected from vitamin A, vitamin D, vitamin E and vitamin K.

The mineral(s) comprise one or more minerals selected from calcium, iron, zinc, vanadium, selenium, chromium, iodine, potassium, manganese, copper and magnesium. The amino acid(s) comprise one or more amino acids selected from lysine, isoleucine, leucine, threonine, valine, tryptophan, phenylalanine, methionine, L-selenomethionine and mixtures thereof.

The oil(s) comprise one or more oils selected from omega-3 fatty acid, flaxseed oil, fish oils, krill oil, essential oils and volatile oils.

The biological activity of *Boswellia* derived compounds/phytochemicals that can be enhanced by bioenhancing agents include extracts of fractions standardized to one or more boswellic acids selected from $\alpha$-Boswellic acid, $\beta$-Boswellic acid, 3-O-acetyl-$\alpha$-Boswellic acid, 3-O-acetyl-$\beta$-Boswellic acid, 3-O-acetyl-11-keto-$\alpha$-Boswellic acid, 11-keto-$\beta$-Boswellic acid and 3-O-acetyl-11-keto-$\beta$-Boswellic acid.

In another aspect, the invention provides bio-enhancing agents selected from *Boswellia* oil (BOIL), *Boswellia* volatile oil (BVOIL) and *Boswellia* low polar gum resin extract (BLPRE) derived from the gum resin of *Boswellia* for enhancing the bioavailability of extracts/fractions particularly standardized to 3-O-acetyl-11-keto-$\beta$-Boswellic acid (AKBA).

In another aspect, the invention provides *Boswellia* derived agents and compositions for enhancing the bioavailability of the phytochemicals derived from *Boswellia* species including but not limited to boswellic acids selected from $\alpha$-boswellic acid, $\beta$-boswellic acid, 3-acetyl-$\alpha$-boswellic acid, 3-acetyl-$\beta$-boswellic acid, 3-acetyl-11-keto-$\alpha$-boswellic acid and 3-acetyl-11-keto-$\beta$-boswellic acid or mixtures thereof.

The *Boswellia* species that can be used for producing the oil (BOIL) or volatile oil (BVOIL) or low polar gum resin extract (BLPRE) from the gum resin comprise one or more species selected from *Boswellia serrata, Boswellia carterii, Boswellia payrifera. Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*.

In another aspect, the invention provides *Boswellia* oil or *Boswellia* volatile oil or *Boswellia* low polar gum resin extract for enhancing the bioavailability of one or more *Curcuma* derived extracts/fractions/components/phytochemicals that can be enhanced by bioenhancing agents include extracts of fractions standardized to selected from curcumin, demethoxycurcumin, bisdemethoxycurcumin, monodemethylcurcumin, bisdemethylcurcumin, tetrahydrocurcumin, tetrahydrodemethoxycurcumin, tetrahydro bisdemethoxycurcumin and ar-turmerone or mixtures thereof.

In another aspect, the invention provides bio-enhancing agents *Boswellia* oil (BOIL), *Boswellia* volatile oil (BVOIL) and *Boswellia* low polar gum resin extract (BLPRE) derived from the gum resin of *Boswellia* for enhancing the bioavailability of extracts/fractions particularly standardized to curcumin or demethoxycurcumin or bisdemethoxycurcumin or mixtures thereof.

In another aspect, the invention provides *Boswellia* derived bioenhancing agents and for enhancing the bioavailability of the one or more phytochemicals derived from *Curcuma* species selected from curcumin, demethoxycurcumin, bisdemethoxycurcumin, monodemethylcurcumin, bisdemethylcurcumin, tetrahydrocurcumin, tetrahydrodemethoxycurcumin, tetrahydro bisdemethoxycurcumin and ar-turmerone or mixtures thereof.

The Curcumin derived components that can be bioenhanced are derived from *Curcuma longa, Curcuma aromatica, Curcuma domestica, Curcuma aeruginosa, Curcuma albicoma, Curcuma albiflora, Curcuma alismatifolia, Curcuma angustifolia, Curcumaelata, Curcuma ferruginea, Curcuma flaviflora, Curcuma yunnanensis* and *Curcuma zedoaria*.

In another aspect the invention provides the representative processes for obtaining *Boswellia* oil (BOIL) comprising:
a) procuring the gum resin of one or more of the plant(s) selected from but not limited to *Boswellia serrata* or *Boswellia carterii* or *Boswellia papyrifera* or mixtures thereof,
b) extraction of the gum resin with a water immiscible organic solvent,
c) filtering the extract carefully to remove the insoluble resin material,
d) washing the organic solvent extract repeatedly with an aqueous alkali solution such as aqueous potassium hydroxide,
e) washing the organic layer with water and brine,
f) evaporating the organic layer under vacuum and high temperature to obtain the oily residue (BOIL).

In another aspect the invention provides a representative procedure for obtaining *Boswellia* volatile oil (BVOIL) comprising:
a) procuring the gum resin of *Boswellia*,
b) separating the Volatile oil component by either steam distillation or distillation under high vacuum and temperature from the said gum resin to obtain BVOIL.
c) alternatively, the BVOIL fraction can be separated from the BOIL fraction described above by vacuum distillation under high vacuum and temperature.

In another aspect, the invention provides a process for producing *Boswellia* low polar gum resin extract (BLPRE) comprising the following steps:
a) extraction of the gum resin of *Boswellia* species with a water immiscible organic solvent and filtering the extract carefully to remove the insoluble resin material,
b) washing the organic solvent extract repeatedly with an aqueous alkali solution such as aqueous potassium hydroxide,
c) washing the organic layer obtained after the alkali wash, with water and brine,
d) evaporating the said organic layer under vacuum and high temperature to obtain the oily residue,
e) removing the volatile compounds from the said oily residue under high vacuum and high temperature to obtain BLPRE.

The water immiscible organic solvent used for extraction can be selected from the group comprising but not limited to 1,2-dichloroethane, hexane, dichloromethane, chloroform, ethyl acetate, n-butanol, methyl iso-butyl ketone (MIBK) or their suitable combination thereof. The alkali solution used for washing the organic solvent extract can be selected from Group-I or Group-II metal hydroxides, which include but not limited to Sodium hydroxide, Potassium hydroxide, Calcium hydroxide and Magnesium hydroxide or mixtures thereof In another aspect, an alternative process for producing BLPRE comprises:
a) preparing the alcohol or hydroalcohol extract of *Boswellia* gum resin,
b) partitioning the alcohol extract between an aqueous alkali solution and a water immiscible organic solvent,
c) separation of the organic solvent layer, followed by evaporation of the solvent to obtain oily residue,
d) removal of volatile compounds from the said oily residue under high temperature and high vacuum to obtain BLPRE.

In another aspect, a further alternative process for producing *Boswellia* low polar gum resin extract (BLPRE) comprise,
a) extracting the gum resin of *Boswellia* species with alcohol or hydro alcohol,
b) evaporating the organic solvent to an optimum level of total solids and then
c) adjusting the pH to the alkaline side, preferably pH 9-12,
d) repeatedly extracting the solution with an organic solvent,
e) evaporating the organic solvent under vacuum and high temperature to obtain the oily residue,
f) evaporating the volatiles from the said oily residue under high vacuum and high temperature to obtain BLPRE.

The alcohol used for extraction can be selected from the group comprising but not limited to methanol, ethanol and propanol or their suitable combination thereof.

Figure 3:
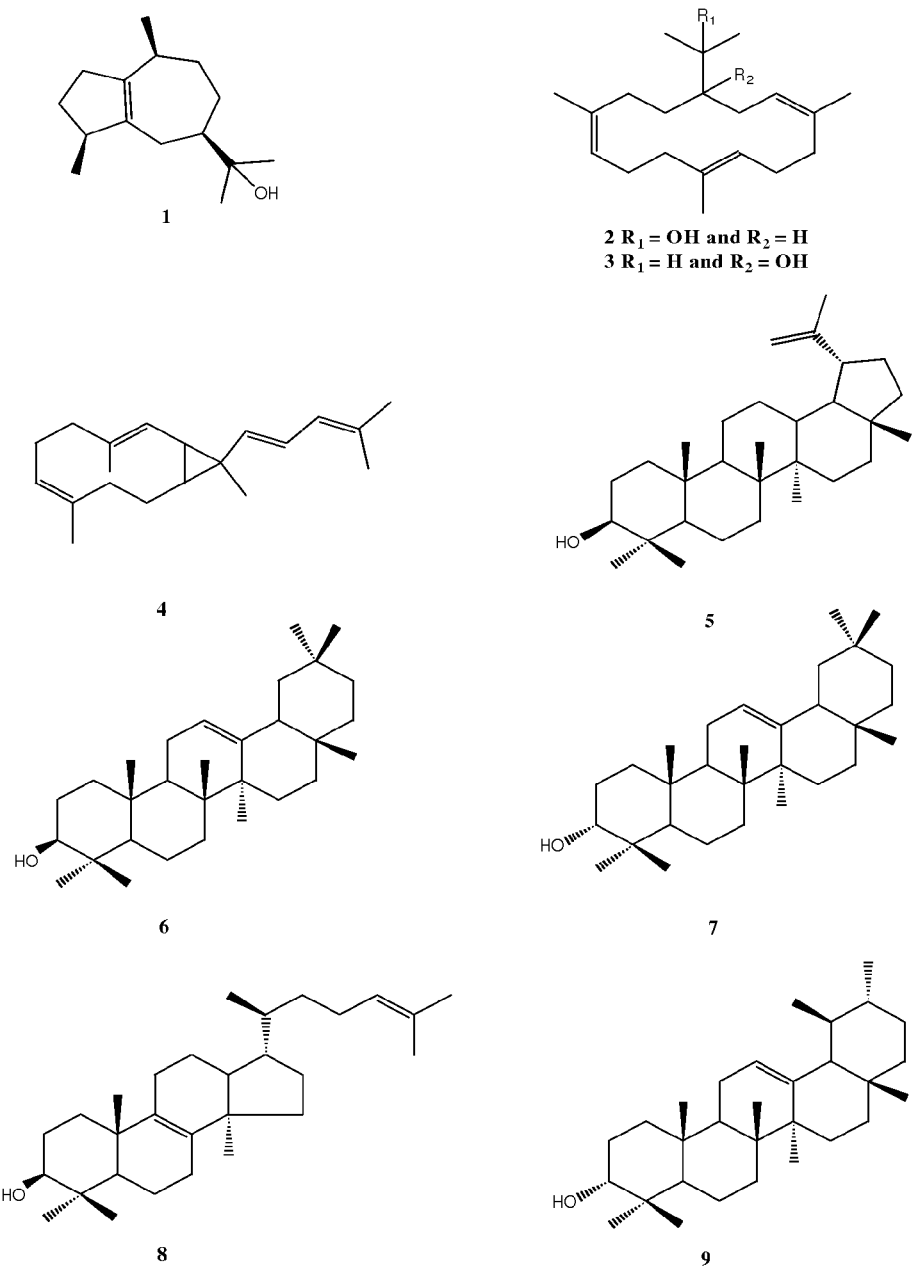
FIG. 3: Figure shows structural formulae 1-9 representing prominent compounds of *Boswellia serrata* low polar gum resin extract (BsLPRE).

In another aspect, the invention provides a *Boswellia* low polar gum resin extract (BLPRE) from *Boswellia serrata*, wherein the said extract comprises one or more phytochemical marker compounds selected from but not limited to guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9), depicted in FIG. 3.

In another aspect, the invention provides a *Boswellia* low polar gum resin extract obtained after selectively removing the acidic and volatile compounds.

The compositions disclosed herein, containing the bioenhancer and a biological agent, are administered through oral, dermal, intravenous, subcutaneous, intra-peritoneal, rectal, intra-muscular or any suitable route in warm blooded animals.

The effective daily dosage of the Bioenhancer(s) in warm blooded animals is in the range of 0.001 to 1500 mg/kg body weight.

The effective daily dosage of the Bioenhancer(s) in warm blooded animals is in the range of 0.01 to 500 mg/kg body weight.

The effective daily dosage of the Bioenhancer(s) in warm blooded animals is in the range of 0.1 to 150 mg/kg body weight.

The effective daily dosage of the Bioenhancer(s) in warm blooded animals is in the range of 1.5-15 mg/kg body weight.

EXAMPLES

Example 1

A Process for Preparation of the *Boswellia* Oil (BOIL):
The process for preparing *Boswellia* oil comprises:
a) procuring the gum resin of one or more of the plant(s) selected from but not limited to *Boswellia serrata* or Boswellia carterii or Boswellia papyrifera or mixtures thereof, b) extraction of the gum resin with a water immiscible organic solvent, c) filtering the extract carefully to remove the insoluble resin material, d) washing the organic solvent extract repeatedly with an aqueous alkali solution such as aqueous potassium hydroxide, e) washing the organic layer with water and brine, and f) evaporating the organic layer under vacuum and high temperature to obtain the oily residue (BOIL).

Example 2

A Process for Preparation of the Boswellia Volatile Oil (BVOIL):

The process for preparing Boswellia volatile oil comprises:

a) procuring the gum resin of one or more of the plant(s) selected from but not limited to Boswellia serrata or Boswellia carterii or Boswellia papyrifera or mixtures thereof, b) separating the volatile oil component by either steam distillation or distillation under high vacuum, low temperature from the said gum resin to obtain Boswellia volatile oil (BVOIL).

Example 3

Preparation of Boswellia serrata Low Polar Gum Resin Extract (BsLPRE):

The Boswellia serrata gum resin (100 g) was dispersed in 600 mL of methyl isobutylketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are then removed from the oily residue under high vacuum at 75-100° C. to obtain Boswellia serrata low polar gum resin extract or BsLPRE as a viscous oil (12 g).

Alternatively, the gum resin (250 g) collected from Boswellia serrata was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain Boswellia oil. The volatile compounds were evaporated from the oil under high vacuum at 75-100° C. to obtain 22 g of BsLPRE.

The BsLPRE was subjected to column chromatography over normal silica gel using solvents of increasing polarity starting from hexane to hexane/ethyl acetate mixtures to ethyl acetate. The identical fractions were combined based on TLC and the combined fractions were subjected individually to repeated column over silica gel using mixtures of hexane/ethyl acetate or hexane/acetone as eluants to obtain pure compounds. Some of the impure fractions were further subjected to preparative HPLC using a reversed phase C18silica column to obtain pure compounds. The structures of individual compounds were established by analyzing the $^1$H NMR, $^{13}$C NMR, DEPT, HSQC and HMBC and mass spectral data and then comparing the data with that of known compounds. Nine of the prominent compounds are identified as guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) as depicted in FIG. I. The pure compounds were then utilized to standardize the Boswellia serrata low polar gum resin extract (BsLPRE) using HPLC method. The novel composition of BsLPRE, evaluated based on analytical HPLC method, along with the retention times (Rt) is summarized in Table 1.

TABLE 1

Composition of Boswellia serrata low polar gum resin extract (BsLPRE)

| S. No | Test substance | $R_t$ in mm | Percentage |
|---|---|---|---|
| 1 | Guiol (1) | 4.5 | 0.96 |
| 2 | Nephthenol (2) | 7.087 | 2.01 |
| 3 | Serratol (3) | 8.027 | 13.32 |
| 4 | Diterpene X (4) | 15.777 | 0.12 |
| 5 | Lupeol (5) | 26.901 | 0.06 |
| 6 | Olean-12-ene-3β-ol (6) | 31.460 | 1.29 |
| 7 | Olean-12-ene-3α-ol (7) | 33.718 | 5.36 |
| 8 | Lanosta-8,24-diene-3α-ol (8) | 35.371 | 1.34 |
| 9 | Urs-12-ene-3α-ol (9) | 37.207 | 4.55 |

Example 4

Preparation of Boswellia carterii Low Polar Gum Resin Extract (BcLPRE):

The Boswellia carterii gum resin (100 g) was dispersed in 600 mL of methyl iso butyl ketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are then removed from the oily residue under vacuum at 75-85° C. to obtain Boswellia carterii low polar gum resin extract or BcLPRE as a viscous oil (9.5 g).

Alternatively, the gum resin (250 g) collected from Boswellia carterii was extracted with methanol (300 mL×3) and the combined methanol extract was concentrated. The residue (50 g) was dissolved in ethyl acetate (400 mL) and extracted thrice with 1N KOH (3×100 mL). The organic layer was washed with water (2×200 mL) and brine (200 mL) and evaporated to obtain Boswellia oil. The volatile compounds were evaporated from the oil under vacuum at 75-85° C. to obtain 17.75 g of BcLPRE.

Example 5

Figure 4:
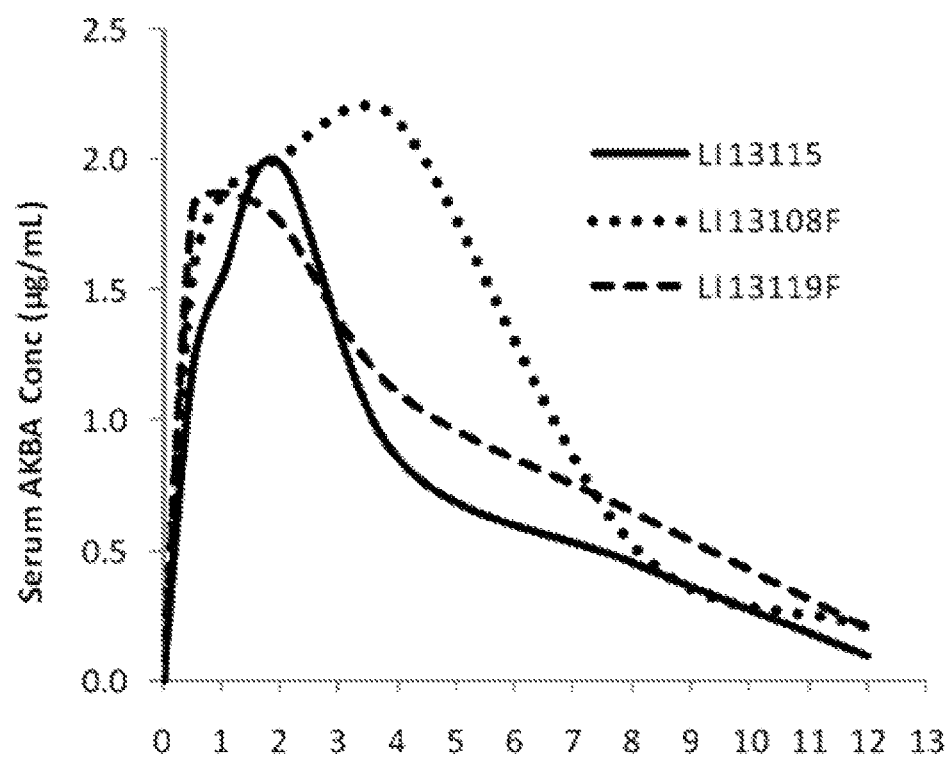
FIG. 4 represents a plot of serum concentration of AKBA after oral administration of the composition LI13108F containing *Boswellia serrata* low polar gum resin extract (BsLPRE) and *Boswellia serrata* extract selectively enriched to 30% 3-O_acetyl-11-keto-β-boswellic acid (AKBA) and composition LI13119F containing *Boswellia serrata* volatile oil fraction (BsVOIL) and *Boswellia serrata* extract selectively enriched to 30% 3-O-acetyl-11-keto-β-boswellic acid (AKBA) to albino rats at doses equivalent to 30 mg/kg of AKBA.

Comparative Bioavailability of 3-O-acetyl-11-keto-β-boswellic Acid (AKBA) from Different Boswellia Products:

Albino Wistar rats were quarantined and healthy rats were selected for the study. The selected animals were acclimatized for 7 days prior to the study initiation in the allocated room Animals employed for the study were randomized into various treatment groups, fasted overnight at free access to water, body weights were noted and individual doses were calculated based on the body weights. Blood samples were collected from all animals prior to oral administration of test products and at 0.5, 1, 2, 4, 8 and 12 hrs after oral administration. Collected blood samples were allowed to clot for 10 min and centrifuged at 4° C. at 1800 g for 10 min. The serum samples were deproteinized with 100 μL TCA (20%) and 1.8 mL of HPLC grade methanol, centrifuged at 4° C. at 1800 g for 10 min and supernatants were subjected to LCMS analysis for total AKBA. The Composition LI 13108F comprising *Boswellia serrata* extract selectively enriched to 30% 3-O-acetyl-11-keto-β-boswellic acid (AKBA) (LI 13115) and *Boswellia serrata* non-volatile oil (BsLPRE) in the ratio 2:1; and composition LI13119F comprising *Boswellia serrata* extract standardized to 30% AKBA and *Boswellia serrata* steam distilled oil (BVOIL) in the ratio 2:1 showed better oral bioavailability with Area under the curve (AUC) 14.08 and 11.23 respectively compared to individual *Boswellia serrata* extract standardized to 30% AKBA (LI 13115) (AUC: 9.825). The bioavailability [in terms of [AUC] of LI 13108F is 43.33% more than LI 13115. The bioavailability of LI 13119F is 14.33% more than that of LI 13115. The serum concentration of AKBA in animals of various treatment groups at various time points was summarized in Table-2. The serum concentration against time was plotted and the results are depicted in FIG. 4.

TABLE 2

Mean Serum AKBA concentration μg/mL

| Time (h) | LI 13115 (Mean ± SE) | LI 13108F (Mean ± SE) | LI 13119F (Mean ± SE) |
| --- | --- | --- | --- |
| 0 | 0.000 ± 0.00 | 0.000 ± 0.00 | 0.000 ± 0.00 |
| 0.5 | 1.200 ± 0.19 | 1.533 ± 0.06 | 1.805 ± 0.21 |
| 1 | 1.545 ± 0.28 | 1.853 ± 0.11 | 1.865 ± 0.32 |
| 2 | 1.980 ± 0.45 | 2.000 ± 0.16 | 1.750 ± 0.26 |
| 4 | 0.850 ± 0.32 | 2.147 ± 0.41 | 1.100 ± 0.07 |
| 8 | 0.452 ± 0.22 | 0.520 ± 0.16 | 0.645 ± 0.13 |
| 12 | 0.095 ± 0.10 | 0.100 ± 0.14 | 0.200 ± 0.20 |
| AUC | 9.825 | 14.0825 (43.33%) | 11.2325 (14.33%) |

Example 6

Comparative Bioavailability of LI01008 and its Composition:

LI3124F1 Animals (Wistar Rats) were acclimatized for 7 days prior to study initiation. Six animals were divided randomly into 2 groups, each comprised of 3 animals. The body weights were noted and doses were calculated based on initial body weights. Animals were treated orally with 450 mg dose of a composition (LI13124F1) containing bisdemethylcurcumin (LI01008) and BsLPRE (LI13115) in 2:1 ratio or 300 mg/kg LI01008 as suspension in 0.5% CMC. Blood samples were collected before treatment and several time intervals after treatment at 0.5, 1, 2, 4, 6, 8 and 12 hours. Collected blood samples were processed in a refrigerated centrifuge and serum samples were deproteinized using HPLC grade methanol, mixed thoroughly and centrifuged to remove precipitated proteins clear supernatants were subjected for LI01008 estimation by HPLC.

Figure 5:
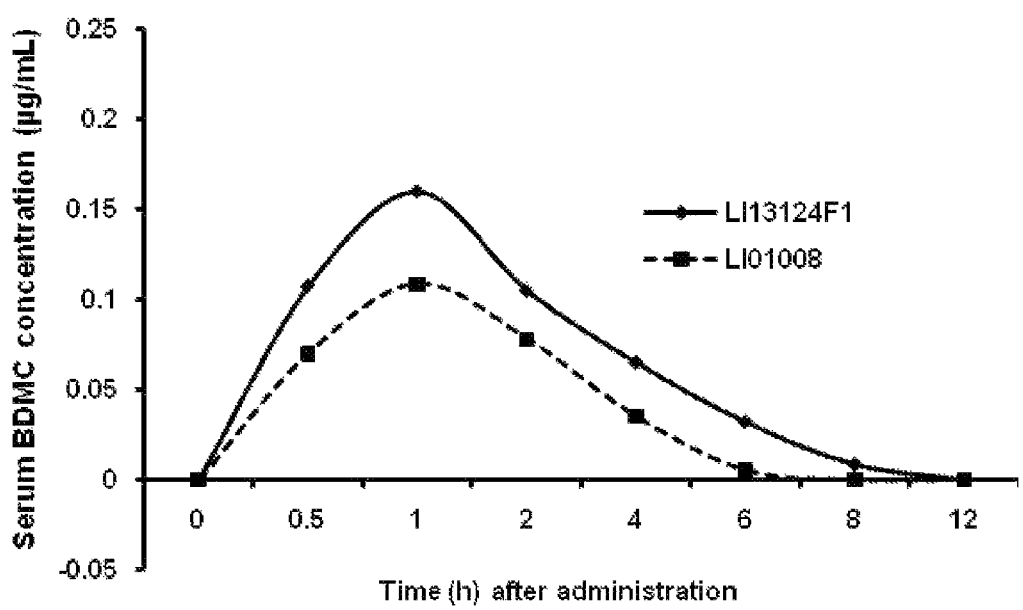
FIG. 5 represents a plot of serum concentration of Bisdemethylcurcumin (LI01008) after oral administration of composition (LI13124F1) containing Bisdemethylcurcumin and *Boswellia serrata* low polar gum resin extract (BsLPRE) in 2:1 ratio at concentration of 450 mg/kg or Bisdemethylcurcumin (LI01008) alone at 300 mg/kg body weight.

The data is summarized in table 3 below. The serum concentration against time was plotted and the results are depicted in FIG. 5.

As per the data, the bioavailability of LI01008 in the composition LI13124F1 is 75% better compared to that when LI01008 is administered alone.

TABLE 3

| S. No | Time after Admn. | LI13124F1 suspension in 0.5% CMC | LI01008 suspension in 0.5% CMC |
| --- | --- | --- | --- |
| 1 | 0 | 0 | 0 |
| 2 | 0.5 | 0.1075 | 0.07 |
| 3 | 1 | 0.16 | 0.1085 |
| 4 | 2 | 0.105 | 0.078 |
| 5 | 4 | 0.065 | 0.035 |
| 6 | 6 | 0.032 | 0.00535 |
| 7 | 8 | 0.0085 | 0 |
| 8 | 12 | 0 | 0 |

It will be appreciated by those of ordinary skilled in the art that changes could be made to the embodiments described above without departing from the broad inventive concept thereof. It is understood, therefore, that this invention is not limited to the particular embodiments or examples disclosed, but is intended to cover modifications within the embodiments and scope of the present invention.

What is claimed is:

1. A method of enhancing the bioavailability of a biological agent, comprising:
    orally administering said biological agent to a subject in combination with an effective amount of a first gum resin extract of a *Boswellia* species which is substantially free of boswellic acids,
    said first gum resin extract of the *Boswellia* species being:
    a water-immiscible organic solvent extract obtained by removing boswellic acids from a *Boswellia* species gum resin extract; or
    a volatile or non-volatile oil obtained by steam distillation of the water-immiscible organic solvent extract; or
    a mixture thereof;
    wherein said effective amount is effective for enhancing the bioavailability of said biological agent,
    wherein the biological agent is a second extract of a *Boswellia* species, and includes one or more boswellic acids selected from the group consisting of α-boswellic acid, β-boswellic acid, 3-O-acetyl-α-boswellic acid, 3-O-acetyl-β-boswellic acid, 3-O-acetyl-11-keto-β-boswellic acid, and 3-O-acetyl-11-keto-α-boswellic acid.

2. The method of claim 1, wherein the second extract of a *Boswellia* species is enriched in 3-O-acetyl-11-keto-β-boswellic acid; and
    the biological agent and the first gum resin extract of a *Boswellia* species are administered in a 2:1 ratio.

3. A method of enhancing the bioavailability of a biological agent, comprising:
    orally administering said biological agent to a subject in combination with an effective amount of a first gum resin extract of a *Boswellia* species which is substantially free of boswellic acids,
    said first gum resin extract of the *Boswellia* species being:
    a water-immiscible organic solvent extract obtained by removing boswellic acids from a *Boswellia* species gum resin extract; or
    a volatile or non-volatile oil obtained by steam distillation of the water-immiscible organic solvent extract; or
    a mixture thereof;
    wherein said effective amount is effective for enhancing the bioavailability of said biological agent,
    wherein the biological agent is an extract of a *Curcuma* species, and includes a curcumin compound selected from the group consisting of curcumin, demethoxycurcumin, bisdemethoxycurcumin, monodemethylcurcumin, bisdemethylcurcumin, tetrahydrocurcumin, tetrahydrodemethoxycurcumin, tetrahydrobisdemethoxycurcumin; and mixtures thereof.

4. The method of claim 3, wherein the curcumin compound and the first gum resin extract of a *Boswellia* species are administered in a 2:1 ratio.

5. A method of enhancing the bioavailability of a biological agent, comprising:
orally administering said biological agent to a subject in combination with an effective amount of a gum resin extract of a *Boswellia* species which is substantially free of boswellic acids,
said gum resin extract of the *Boswellia* species being:
a water-immiscible organic solvent extract obtained by removing acidic compounds from a *Boswellia* species gum resin extract; or
a volatile or non-volatile oil obtained by steam distillation of the non-acidic water-immiscible organic solvent extract; or
a mixture thereof;
wherein said effective amount is effective for enhancing the bioavailability of said biological agent;
wherein the biological agent includes at least one of:
one or more boswellic acids selected from the group consisting of α-boswellic acid, β-boswellic acid, 3-O-acetyl-α-boswellic acid, 3-O-acetyl-β-boswellic acid, 3-O-acetyl-11-keto-β-boswellic acid, and 3-O-acetyl-11-keto-α-boswellic acid; and
a component selected from the group consisting of curcumin, demethoxycurcumin, bisdemethoxycurcumin, monodemethylcurcumin, bisdemethylcurcumin, tetrahydrocurcumin, tetrahydrodemethoxycurcumin tetrahydrobisdemethoxycurcumin and mixtures thereof.

6. The method of claim 5, wherein said *Boswellia* species is selected from the group consisting of *Boswellia serrata, Boswellia carterii, Boswellia papyrifera*, and mixtures thereof.

7. The method of claim 5, wherein said non-acidic gum resin extract is administered in an amount which is effective for enhancing the bioavailability of said biological agent in a warm blooded animal in need thereof.

8. The method of claim 5, further comprising administering an antioxidant comprising one or more ingredients selected from the group consisting of vitamin A, vitamin C, vitamin E, alpha-carotene, trans-beta-carotene, betacryptoxanthin, lycopene, lutein, zeaxanthin, pine bark bioflavanols complex, germanium, selenium and zinc.

9. The method of claim 5, further comprising administering a vitamin comprising:
a water-soluble vitamin selected from the group consisting of vitamin B1, vitamin B2, niacinamide, vitamin B6, vitamin B12, folic acid, vitamin C, and mixtures thereof;
a fat-soluble vitamin selected from the group consisting of vitamin A, vitamin D, vitamin E and vitamin K, and mixtures thereof; or
a mixture of said water-soluble vitamin and said fat-soluble vitamin.

10. The method of claim 5, further comprising administering a mineral comprising one or more minerals selected from the group consisting of calcium, iron, zinc, vanadium, selenium, chromium, iodine, potassium, manganese, copper, and magnesium.

11. The method of claim 5, further comprising administering an amino acid comprising one or more amino acids selected from the group consisting of lysine, isoleucine, leucine, threonine, valine, tryptophan, phenylalanine, methionine, and 1-selenomethionine.

12. The method of claim 5, further comprising administering an oil comprising one or more oils selected from the group consisting of omega-3 fatty acids, flaxseed oil, fish oils, essential oils and volatile oils.

13. The method of claim 5, wherein said *Boswellia* species is selected from the group consisting of *Boswellia ameero, Boswellia bullata, Boswellia dalzielii, Boswellia dioscorides, Boswellia elongata, Boswellia frereana, Boswellia nana, Boswellia neglecta, Boswellia ogadensis, Boswellia pirottae, Boswellia popoviana, Boswellia rivae, Boswellia sacra* and *Boswellia socotrana*.

14. A method of enhancing the bioavailability of a biological agent, comprising:
orally administering said biological agent to a subject in combination with an effective amount of a non-acidic gum resin extract of a *Boswellia* species,
said non-acidic gum resin extract of the *Boswellia* species being a water-immiscible organic solvent extract of the gum resin of said *Boswellia* species;
said water-immiscible organic solvent extract comprising serratol, olean-12-ene-3α-ol, and urs-12-ene-3α-ol, and substantially no boswellic acids;
wherein said effective amount is effective for enhancing the bioavailability of said biological agent;
wherein the biological agent includes at least one of:
one or more boswellic acids selected from the group consisting of α-boswellic acid, β-boswellic acid, 3-O-acetyl-α-boswellic acid, 3-O-acetyl-β-boswellic acid, 3-O-acetyl-11-keto-β-boswellic acid, and 3-O-acetyl-11-keto-α-boswellic acid; and
a component selected from the group consisting of curcumin, demethoxycurcumin, bisdemethoxycurcumin, monodemethylcurcumin, bisdemethylcurcumin, tetrahydrocurcumin, tetrahydrodemethoxycurcumin, tetrahydrobisdemethoxycurcumin and mixtures thereof.

* * * * *